United States Patent [19]
Tsimerman

[11] Patent Number: 5,803,729
[45] Date of Patent: Sep. 8, 1998

[54] CURING LIGHT

[75] Inventor: Efraim Tsimerman, 480 Queens Quay West, Apt. 903W, Toronto, Ontario, Canada, M5V 2Y5

[73] Assignee: Efraim Tsimerman, Toronto, Canada

[21] Appl. No.: 682,489

[22] Filed: Jul. 17, 1996

[51] Int. Cl.⁶ .............................. A61C 19/00; G02B 6/42
[52] U.S. Cl. ........................... 433/29; 362/294; 362/318; 607/93; 606/2
[58] Field of Search ........................ 433/29, 229; 362/32, 362/294, 318, 373; 606/2; 607/88, 92, 93

[56] References Cited

U.S. PATENT DOCUMENTS

| | | | |
|---|---|---|---|
| 1,550,197 | 8/1925 | Berry | 607/93 |
| 1,590,283 | 6/1926 | Catlin | 607/93 |
| 1,677,016 | 7/1928 | Berry | 607/93 |
| 2,227,422 | 1/1941 | Boerstler | 607/93 |
| 3,712,984 | 1/1973 | Lienhard | 607/93 |
| 4,229,658 | 10/1980 | Gonser. | |
| 4,729,621 | 3/1988 | Edelman | 607/93 |
| 5,184,044 | 2/1993 | Thomas | 313/638 |
| 5,290,169 | 3/1994 | Friedman et al. | 433/29 |
| 5,312,249 | 5/1994 | Kennedy | 433/29 |
| 5,554,855 | 9/1996 | Ueno | 250/455.11 |

FOREIGN PATENT DOCUMENTS

| | | | |
|---|---|---|---|
| 0 581 226 | 2/1994 | European Pat. Off. . | |
| 2808045 | 9/1979 | Germany | 433/229 |
| 3424344 | 1/1986 | Germany | 433/29 |
| 35 23 243 | 1/1987 | Germany . | |
| 35 34 342 | 3/1987 | Germany . | |
| 3534342 | 3/1987 | Germany | 433/29 |
| 3820413 | 11/1989 | Germany | 433/29 |
| 2044908 | 10/1980 | United Kingdom | 607/93 |

*Primary Examiner*—Ralph A. Lewis
*Attorney, Agent, or Firm*—Bereskin & Parr

[57] ABSTRACT

A light curing gun for dental filling material includes a conical light concentrator element and a water filed chamber between the light source and the concentrator element. The water increases the collection of light as well as cooling the concentrator and filtering out light in the infrared portion of the spectrum. A water cooling jacket may also be provided around the light source and may be coupled to the water window so that water can be circulated through both the window and the water jacket.

8 Claims, 6 Drawing Sheets

CURING LIGHT

FIELD OF THE INVENTION

This invention relates generally to apparatus for light curing of materials that contain a photoactivator, for example dental filling materials.

BACKGROUND OF THE INVENTION

Traditionally, tooth coloured dental filling materials have relied on chemical activation for hardening. Photoactivators were introduced initially for use with ultra-violet curing lights. Concern over the use of ultra-violet light as well as poor efficacy of ultra-violet light in effecting curing (polymerization) led to the development of Blue light activated materials and Blue (visible) light curing units.

Advantages claimed for light curing included complete operator control of working time. In other words, the operator could spend as much time as was required to manipulate and sculpt the filling material; only when curing was desired, would the filling be exposed to the light. Reduced treatment time was also claimed as an advantage. Chemical activation would normally result in curing in three minutes after the components were mixed whereas light curing would take only about 40 seconds.

As the dental profession switched to light curing it was discovered that both of these claims were somewhat fallacious. First, the photosensitivity of light cured materials to ambient light and particularly to the overhead dental light negated the claim of unlimited working time. These materials, particularly in their lighter shades, would begin to harden during manipulation and sculpting following placement. Further, since light curing had a limited depth of cure (typically 2–3 mm, depending on the intensity of the light), the photoactivated materials would have to be placed in small increments. In large size fillings, the total placement and curing time would by far exceed the curing time of chemically activated materials. In some current procedures, the recommended light curing time for one tooth can reach 6–7 minutes.

The speed of curing dental materials can be increased by substantially raising the light output from a curing light. The average output of existing models is 500–600 mW/cm$^2$, with the top models approaching 750 mW/cm$^2$.

The universal photoactivator in light cured dental materials is camphorquinone. Its peak absorption of light is at 468 nM. The absorption falls sharply below 450 nM and above 490 nM. Interferential filters employed in today's curing lights allow transmission at wavelengths in a range of 400–500 nM. Accordingly, the energy of light output is spread over this portion of the spectrum and a significant portion of the energy transmitted is ineffective in the curing process.

The main impediment to increasing light output is the difficulty in collecting and transferring the light energy to the target without significant losses. Conventional optical designs use a halogen light bulb (typically 35–100 W), equipped with an elliptical reflector. The light is transmitted (via the interferential filter) to the input end of a fiberoptic light guide with a typical halfangle of ray acceptance of 30–40 degrees. Such designs are acceptable for point light sources (i.e. an extremely small filament). However, powerful lamps require large filaments and usually have large optical losses.

DESCRIPTION OF THE PRIOR ART

The patent literature contains a number of examples of prior proposals for dental curing lights. Examples are:

U.S. Pat. Nos:
 3,712,984 (Lienhard)
 4,298,806 (Herold)
 4,836,782 (Gonser)
 5,147,204 (Patten et al.)
 5,2,90,169 (Friedman et al.)
 5,397,892 (Abdelqader)
Other prior art patents of interest are:
U.S. Pat. Nos:
 3,596,125 (Seigel)
 4,792,692 (Herold et al.)
 5,192,863 (Kavehrad et al.)
 5,312,249 (Kennedy)
 5,471,129 (Mann)

The Gonser patent (U.S. Pat. No. 4,836,782) shows a proposal for a dental curing light that includes "light condensing means" in the form of a hollow truncated cone with a reflective inner surface for reducing the divergence of the light source.

SUMMARY OF THE INVENTION

An object of the present invention is to provide an apparatus for curing light curable materials intended to allow the use of larger, more powerful light sources than have hitherto been practicable.

The apparatus provided by the invention includes a source of light, non-imaging light concentrator means having an input end for receiving light from the source and an output end through which a concentrated beam of light can leave the concentrator. Means is provided for mounting at the output end of the concentrator, a light guide having an input end for receiving a concentrated light beam from the concentrator, and an output end for directing light to a material to be cured. The light concentrator means includes a chamber for a liquid that is selected to both cool the concentrator and filter from the light passing from the light source to the concentrator, light of a wavelength above a predetermined threshold.

Light rays entering the liquid will be refracted inwardly (towards the optical axis of the ray "bundle") thereby increasing light collection. The liquid will also provide a cooling effect and filter out light above the threshold of light that is useful in the curing process. As a result, the apparatus of the invention allows the use of more powerful light sources than have hitherto been practical. In other words, by virtue of its cooling effect, the liquid protects the concentrator from the damaging effects of a larger light source. The liquid also removes "surplus" light energy and increases light collection. Use of a more powerful light source is thereby justified in that the extra light energy is collected rather than being lost in transmission. At the same time, the concentrator ensures that the useful light energy is properly directed for use in the curing process.

Where Blue light curing is employed, water is the preferred liquid in that it has been found to filter out most of the infrared radiation in the spectrum (above about 1300 nM). Water has the further advantage that water soluble materials that are useful for modifying the characteristics of the filter can be used in the chamber. For example, copper chloride solution, copper sulfate solution, calcium chloride solution or a combination of copper chloride and calcium chloride can be used.

Additionally, the light source may be provided with a cooling water jacket. Water used in the jacket can also be circulated through the chamber, for example, in a circulation circuit in which heat can be dissipated from the water during circulation.

BRIEF DESCRIPTION OF DRAWINGS

In order that the invention may be more clearly understood, reference will now be made to the accompanying drawings which illustrate a particular preferred embodiment of the invention by way of example, and in which:

FIG. 4 comprises views denoted a) and b) which are respectively a longitudinal cross-sectional view through a preferred form of light guide for use in the curing gun of the invention, and a transverse cross-sectional view on line b—b of FIG. 4a; and, FIGS. 5 to 8 are longitudinal sectional views through alternative forms of light concentrator element that may be used in the curing gun of the invention.

DESCRIPTION OF PREFERRED EMBODIMENT

Figure 1:
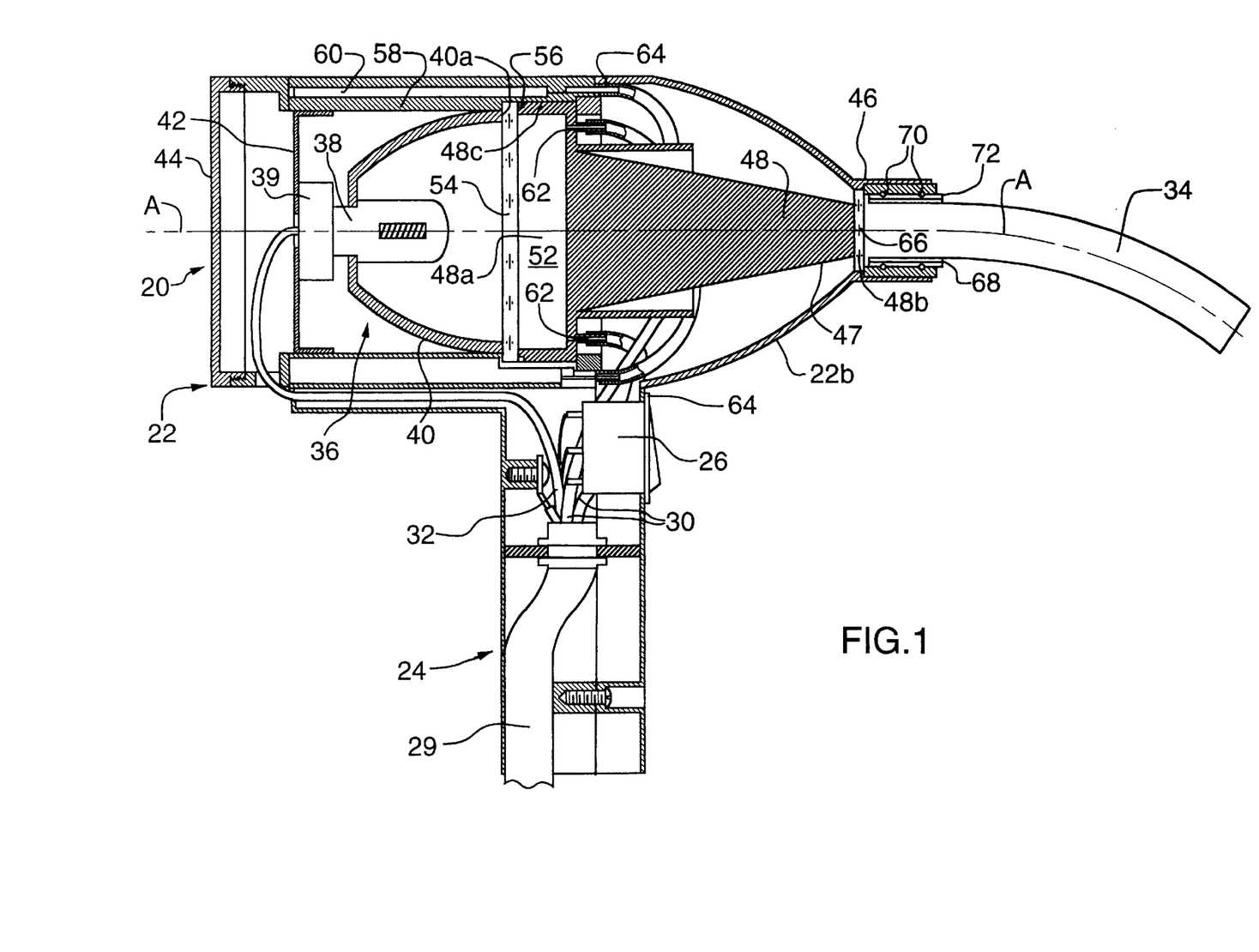
FIG. 1 is a vertical sectional view through a light curing gun for dental purposes, in accordance with a preferred embodiment of the invention.

Referring first to FIG. 1, a curing light "gun" for dental filling material is generally indicated by reference number 20 and includes a housing 22. The housing has a handle 24 which provides a "pistol" grip, and which incorporates a "trigger" switch 26. A flexible conduit 28 extends through and outwardly of the handle and encloses tubes 30 that are connected to an external water pump (not shown) and electrical cables 32 that are connected externally to a power supply (also not shown). Handle 24 allows the curing light to be held and manipulated by the dentist in use.

Housing 22 includes a cylindrical body part 22a and a dome-shaped front part 22b that extends forwardly from the body part. A solid light guide 34 protrudes from the forward end of the housing. Within the housing is a light source 36 comprising a halogen bulb 38 and an elliptical reflector 40. Bulb 38 is a conventional halogen bulb and is mounted generally at the focal point of the reflector. The reflector is positioned to direct the light forwardly towards the light guide 34. Bulb 38 is plugged into a socket 39 which is supported by a removable retaining plate 42. Housing 22 has a removable end plate 44 for allowing access to the bulb.

Bulb 38 and reflector 40 are disposed symmetrically with respect to a longitudinal axis A—A of housing 22. A sleeve 46 at the forward end of the housing receives the light guide and is also symmetrical about axis A—A so that the light guide 34 itself will be centered on that axis. The light guide has an input end 34a for receiving light from the light source, and an output end 34b for directing light to the target material to be cured.

The curing gun includes non-imaging light concentrator means 47 between the light guide 34 and the light source 36, including a concentrator element 48 in the form of a solid of frusto-conical shape. The concentrator element is positioned symmetrically about axis A—A with its wide or base end 48a facing the light source 36 for receiving light from the source, and its narrower (output) end 48b remote from the light source and in "register" with the light guide 34. Light concentrator element 48 may be made of glass, or an appropriate plastic material such a polycarbonate, or polymethylmethacrylate.

The light concentrator means 47 also includes a chamber 52 at the input end 48a of the concentrator element. Chamber 52 receives a liquid that is selected to cool the concentrator element and filter from the light passing from the light source to the concentrator element, light of a wavelength above a predetermined threshold, and to increase light collection from the source. In this particular embodiment, chamber 52 is filled with water and forms a "water window". Light above a wavelength of about 1300 nM is filtered by the water from the light that is transmitted to the concentrator element.

In this particular embodiment, chamber 52 is defined between a glass panel 54 that is held against an outer edge 40a of reflector 40 (at its point of largest diameter) and an annular extension 48c around the perimeter of the input end of concentrator element 48. An "O" ring seal 56 is provided between the glass panel 54 and the outer edge of extension 48c.

The main body part 22a of housing 22 has a double wall for providing a water jacket around the light source 36. As seen in FIG. 1, the inner wall is denoted 58 and the water jacket space is indicated at 60. Water is circulated through space 60 and through chamber 52 by way of tubes, two of which have previously been referred to and designated by reference numeral 30. The tubes are connected to chamber 52 by ports indicated at 62 and to the water jacket 60 by ports indicated at 64. While the precise direction of water flow is not believed critical, the water can, for example, flow first upwardly through chamber 52, then downwardly into the bottom of the water jacket, leaving through the top of the water jacket and flowing out through the conduit 28 to the external pump mentioned previously. Separate water flow circuits could of course be provided, as could a heat exchanger or reservoir for aiding dissipation of heat from the cooing water at a location remote from the curing gun itself.

Briefly, light rays from bulb 38 are directed by reflector 40 forwardly through chamber 52 where the "water window" removes heat and filters out light in the infrared range, i.e. above about 1300 nM. The light rays are refracted towards axis A—A in passing through the liquid, increasing light collection (as compared with a similar arrangement without the water window), are concentrated in concentrator element 48 and then delivered into the light guide 34.

At the output end 48b of concentrator 48 is an interferential filter 66 of the type conventionally used in curing guns, but with a much narrower band of transmittance (460–490 nM). The filter is located at the inner end of the sleeve 46 on the front part 22b of housing 22 and is held in place by a tube 68 that is screw threaded into sleeve 46. This allows the filter to be replaced simply by removing tube 68.

The light guide 34 is of course also replaceable. Normally, it will be "throw away" item that is discarded after each patient use. The inner end of the light guide is simply a sliding fit inside tube 68 and is held in place by "O" rings 70.

Figure 4A:
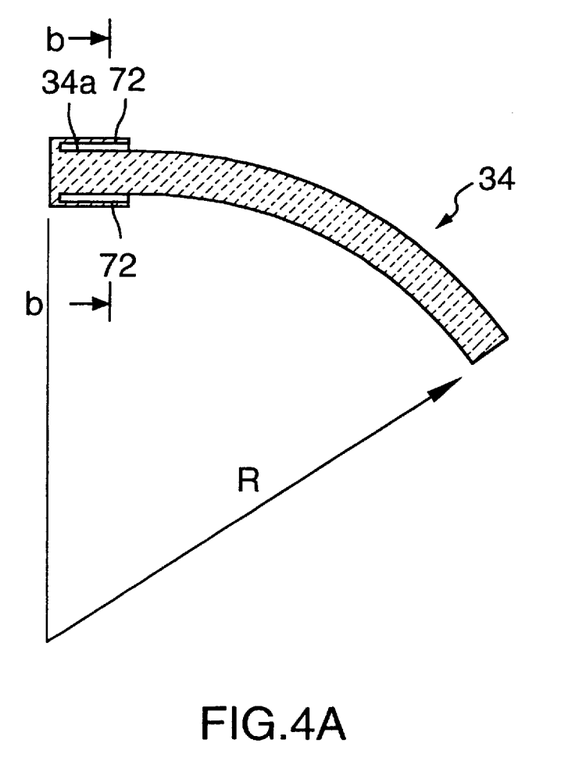
Figure 4B:
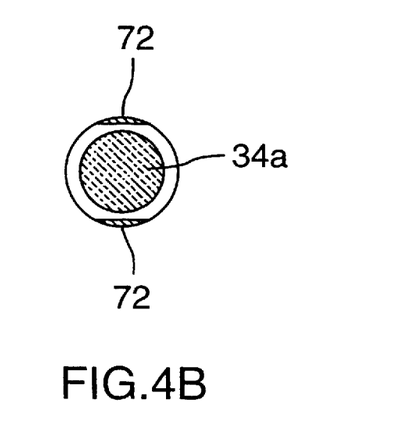

FIG. 4 comprises views denoted a) and b) which show respectively a longitudinal sectional view and a transverse sectional view through a preferred form of light guide 34 for use in the curing gun of the invention. It is, however, to be understood that other forms of light guides can be used, including conventional guides.

Light guide 34 originates as a straight cylindrical section 34a which is provided at its input end with two small flaps 72 for retention inside the tube 68 of the curing gun. The light guide then continues as a curved section 34b towards the output end of the light guide. The practically reasonable radius of curvature (R) of section 34(b) to minimize light losses and yet allow access to tooth surfaces inaccessible by a straight guide is determined by the index of refraction of the material from which the light guide is made and the diameter of the guide. Preferred ranges for the diameter of the light guide is 2–14 mm and for the radius of curvature (R) is 4–20 cm. The length of the straight section 34a may vary but the section extends at least to the outer ends of the flaps 72.

Examples of suitable materials for the light guide are glass, polycarbonate, polymethylmethacrylate.

The light guide can be made of other materials and in other sizes and curvatures or could be completely straight.

The design of a curing light in accordance with the invention allows the use of a bulb 38 of higher output than would otherwise be possible. This in turn allows the use of an interferential filter (filter 66) with a narrowly defined transmittance band (460–490 nM), which is at the peak of the light absorption capability of the camphorquinone material (470 nM) that is used as a photoactivator in light cured dental materials. Not only does this eliminate wasted energy, and consequently heat that would otherwise reach the patient's tooth, it still allows the curing process to be accelerated significantly as compared with conventional curing processes, possibly by as much as 80–90%. It may also be possible that new and less photo-sensitive materials can be developed to allow significantly greater control over working time and sculpturing under full overhead illumination in a dental office.

Figure 2:
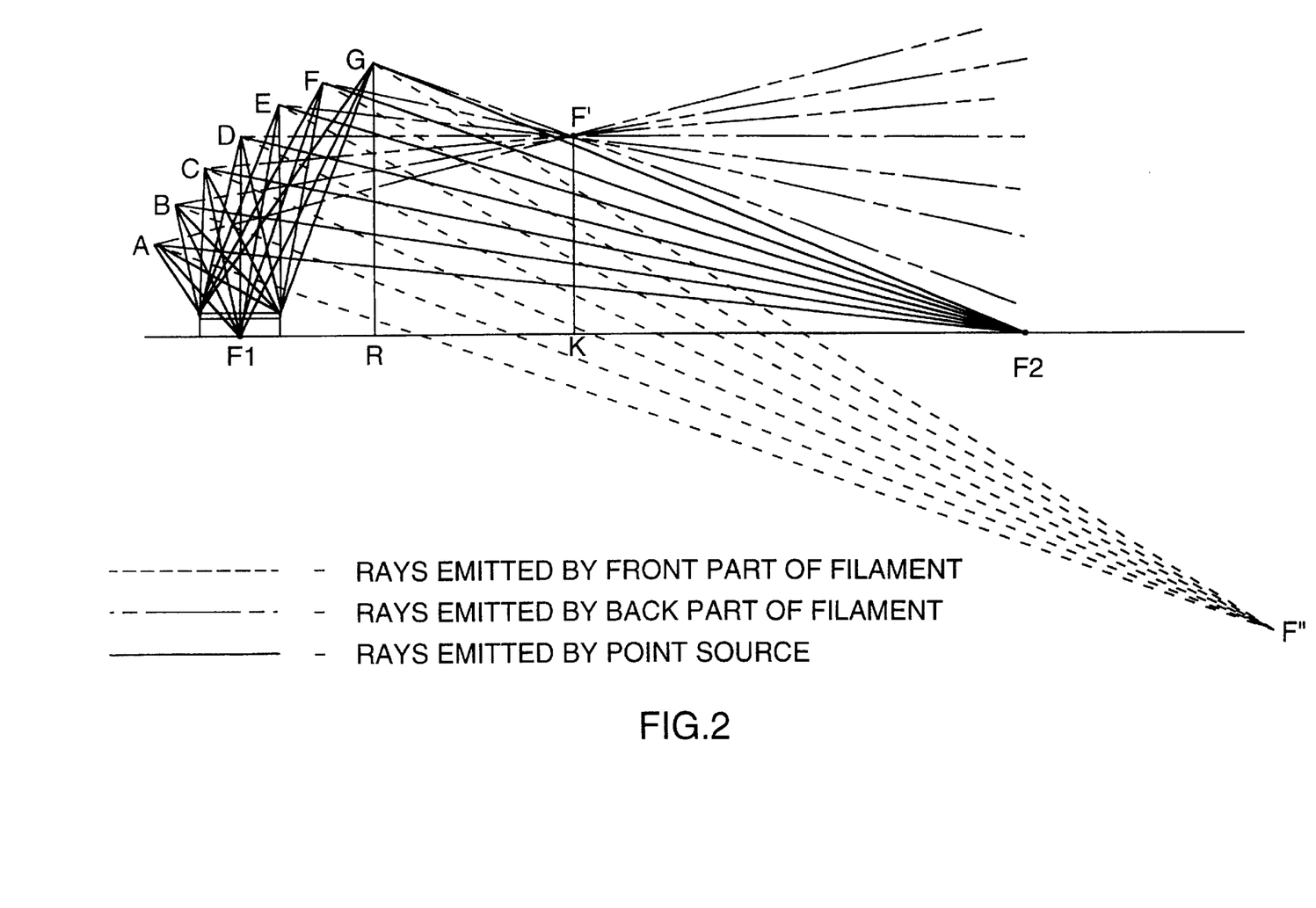
FIGS. 2 and 3 are ray tracings illustrating the advantageous effects that may be achieved in accordance with the invention.
Figure 3:
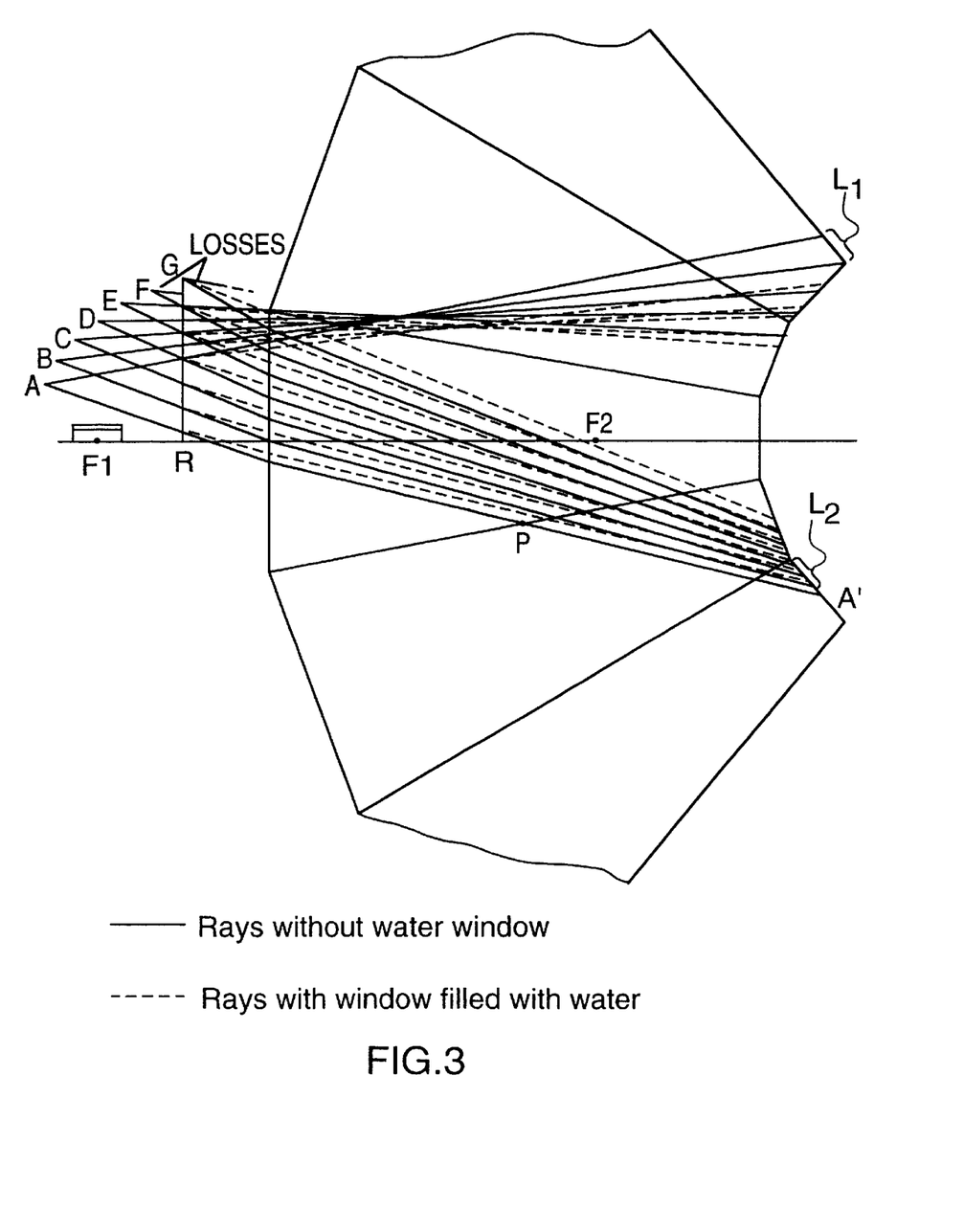

Reference will now be made to FIGS. 2 and 3 in describing the transmission of light rays through the concentrator 48 of the curing gun.

FIG. 2 shows ray tracing for meridional rays emitted by a cylindrical bulb filament having a diameter of 3.5 mm and a length of 6 mm. Filaments of this type are used in 300–500 W halogen bulbs. The filament is shown situated at the first focal point of an elliptical reflector. The distance between two foci is 60 mm. The diameter of the reflector's outer edge is 42 mm.

The solid lines represent rays emitted by a point source, placed at the focal point F1. These rays are projected by the reflector's elliptical surface (represented by points A, B, C, D, E, F, G) to the second focal point F2.

The dashed lines and the chain-dotted lines represent rays emitted by the frontmost and rearmost points of the filament respectively. As is seen from the drawing, these rays arrive at points F' and F". Rays emitted by all other points of the filament surface are focused on the line joining F' and F'". Therefore, there is no true focusing in this case. The beam's minimal radius (a perpendicular line joining F' with the optical axes at K) is about 15 mm. Therefore the light guide entrance should have a commensurate diameter i.e. 30 mm (which clearly is impractical in this application). A more reasonable size of guide will lead to inevitable power losses. A conventional light guide with an entrance diameter of 10 mm will decrease the light intensity up to 9 times, as compared with the ideal of 30 mm.

In accordance with the invention, the light beam diameter is decreased by the use of the non-imaging concentrator element 48; in the illustrated embodiment this is a solid transparent cone, employing the principle of total internal reflection. The first condition for a functional concentrator is:

$$D \sin A = d \sin a$$

where

D—entrance aperture of the cone;

A—angle of incidence of input ray;

d—exit diameter of the cone;

a—angle of emmitance of output ray (ref. 4)

The maximum incident angle for the rays reflected by an elliptical reflector onto the vertical plane GR (FIG. 2) is approximately 24 degrees. Choosing the exit cone diameter d to equal 10 mm and the angle of emmitance 60 degrees; D=d*sin 60/sin 24=21 mm.

The second important condition is:

$$90-(B+(2*m-1)*C) > Q$$

$$\sin B = \sin A/n$$

where

B—angle of refraction of input ray;

C—cone halfangle;

Q—critical angle (sin Q=1/n);

n—refraction index of cone material;

m—number of reflections of the incident ray from the cones walls

The second condition simply means that if, after a few reflections, the angle of incidence becomes lesser than the critical angle, light rays start to escape from the cone through side walls.

FIG. 3 is a "developed" view of concentrator 48.

Concentrator element 48 may be made from different materials (e.g. polymethylmethacrylate, polycarbonate or glass). Modified shapes including exponential and stepped cones may also be used. Refractive indices of these materials vary from 1.45 to 1.8. The cone halfangles C also vary from 7 to 12 degrees. The cone shown in FIG. 3 was made from polymethylmetacrylate with a refraction index of 1.45, halfangle C=10 degrees, Z (diameter of the input end 48a of the cone)=32 mm, Q=46 degrees and m should not exceed 2.

The cone should be positioned in such a way that the most divergent ray AA' will strike the cone's wall at point P where the cone's diameter equals 21 mm (FIG. 3—first condition—see calculation for D in first condition). It is clear that some rays escape through the cone's walls or do not get into the "exit" aperture (48b).

In FIG. 3, losses due to rays escaping through the sidewall as they strike it at an angle less than the critical angle for the material are indicated at $L_1$. $L_2$ indicates losses due to rays which strike the exit plane at a very high angle and are reflected back into the cone and subsequently are lost by escaping through a sidewall or the entrance plane.

The performance of the concentrator will be adversely affected by overheating due to heat transfer from the light bulb. Without the "water window" 52 the cone will start to melt (or fracture in the case of glass) after 30 seconds of illumination.

Both of these problems are alleviated by using the water window 52 between the cone base and the reflector's rim GR. The water bends the light rays further toward the optical axis F1–F2, thereby increasing light collection (dotted lines in FIG. 3) by decreasing the radius of the beam, which in turn allows the rays entering the cone to strike the walls of the cone closer to the exit, thereby allowing a greater number of rays to arrive at the exit surface after two reflections.

It is important to note that for rays with an angle of incidence higher than 14 degrees, the third reflection leads to their escape through the side wall due to them exceeding the critical angle of 46 degrees. The same mechanism increases collection of rays from the beam emitted by the bulb forward, i.e. not reflected by the reflector.

Despite the fact that almost all halogen light bulb reflectors have a multi-layer dichroic coating which reflects the blue part of the spectrum and transmits the red, only a few of them block reflection in the I.R. region (especially >1200 nM). I.R. emission transferred by the light guide could cause unnecessary heating of tooth tissue. As noted previously, water is a very efficient I.R. filter. The thickness of the water layer preferably should be in a range of 5–21 mm. A 10 mm water layer is completely opaque for wavelengths higher than 1300 nM.

Another useful feature of the water window 52 is that it provides the opportunity to use coloured water-soluble substances (e.g. $CuSO_4$) as an order separating filter in combination with a bandpass interferential filter. This can achieve a decrease in the heat load on the tooth without significant curing speed loss. Also the addition of various salts (example: $CaCl_2$) increases the refraction index of the window media and by this increases light collection.

It should also be noted that by using a water window 52 to protect the cone from overheating, it is possible to significantly reduce losses (e.g. as much as 10%) due to reflection in comparison with a similar system without water, where a heat absorbing glass is used to protect the concentrator element. It is known that the reflection index of transparent media equals:

$$R=(n-1)^2/(n+1)^2$$

where n—refraction index of transparent material.

The loss due to reflection of light passing from air to glass is approximately 5% on each surface. Because of close values of refraction indices for water, glass and acrylic the relative refraction index for light passing from glass to water and from water to acrylic is very close to 1. Therefore the reflections on these boundaries are very low.

In practical tests, it was found that a prototype curing gun in accordance with the preferred embodiment of the invention as shown in FIG. 1 had a light output equal to 2,800 mW/cm². This compares with an average power output of 500–600 mW/cm² for existing models. The prototype was equipped with a 9.5 degree cone having a diameter of 10 mm at the output end and 32 mm at the inner end, with a "water window" 8 mm thick and a 3 mm thick glass panel (54). The gun had an interferential filter with a band-pass of 100 nM (400–500 nM) and an acrylic light guide of a diameter of 10 mm and a curvature of 100 mm radius. The gun was fitted with a 340 W bulb.

It should also of course be understood that the description given above refers to a particular preferred embodiment of the invention and that, while a number of modifications have been indicated previously, others are possible within the broad scope of the invention. For example, the feature of a "water window" (52) could be used without water cooling of the light source. It should also be noted that, while a particular form of non-imaging light concentrator element has been described, other equivalent devices may be used within the broad scope of the invention, for example, a hollow conical light concentrator of the form described in the Gonser patent referred to previously. The liquid filled chamber or "water window" 52 could also be incorporated as part of the concentrator element itself. For example, concentrator element could be hollow and filled with liquid.

FIGS. 5 to 8 illustrate alternative forms of concentrator element that may be used within the broad scope of the invention. It should also be noted that, while FIGS. 5 to 8 show hollow structures, structures of the same form but solid and with or without mirrored walls could be used with a liquid filled chamber as chamber 52.

Figure 5:
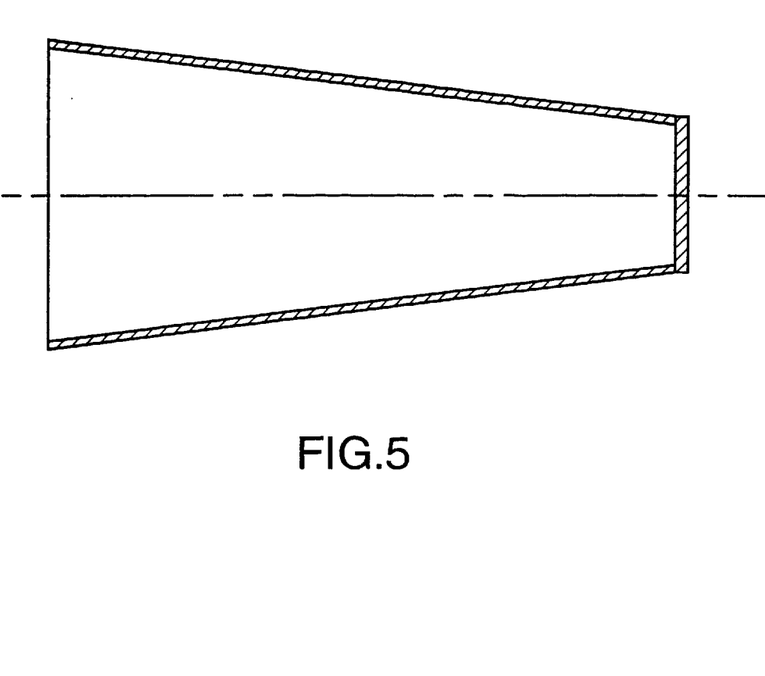

FIG. 5 shows a concentrator of hollow truncated conical form. This form of concentrator will be transparent or with wall surfaces that are mirrored towards the interior. The concentrator can be liquid filled or used with a separate "water window".

Figure 6:
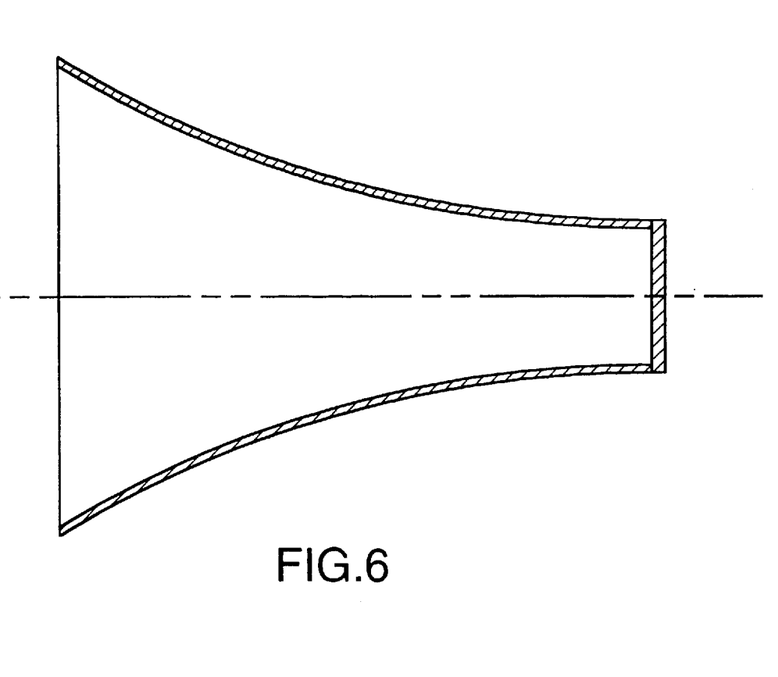

FIG. 6 shows a transparent exponential cone which can also have mirrored walls and be filled with liquid or used with a separate water window.

Figure 7:
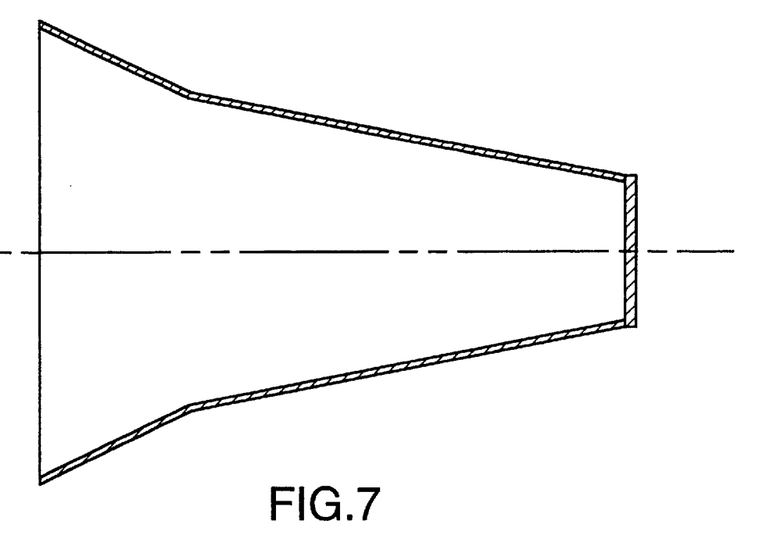

FIG. 7 shows a stepped cone which can have transparent or mirrored walls and which again can be liquid filled or used with a separate water window.

Figure 8:
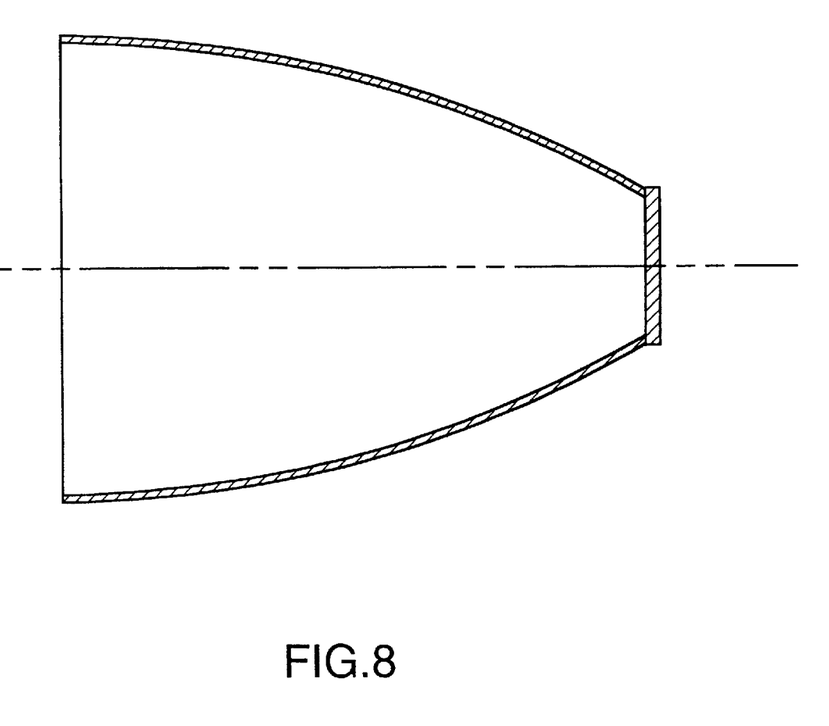

Finally, FIG. 8 shows a concentrator of compound parabolic shape, which is also transparent or with mirrored walls and can be liquid filled or used with a separate water window.

Referring to the interferential filter 66, it should also be noted that the interferential filter could alternatively be used at the input end of the concentrator on 48 between the concentrator element and the water window 52. The interferential filter is then directly cooled by the water, which may have some advantage in terms of avoiding heat damage to the filter. Also, heat load on the concentrator element is then reduced because only the portions of the wavelengths of light that are passed by the interferential filter will then reach the concentrator element 48. In other words, the heat load on the concentrator element is reduced.

Also, while the description refers to a Blue light curing gun, the invention may be applicable in an apparatus that works in other parts of the spectrum. Other liquids having light filtering characteristics can be used. For example, a solution containing both nickel sulphate and cobalt chloride ($Ni_2$ $SO_4$ and $CoCl_2$) will transmit light in the ultraviolet portion of the spectrum while absorbing visible light and part of the infrared portion of the spectrum. A solution containing potassium bichromate ($K_2Cr_2O_7$) will transmit light in the yellow and red portions of the spectrum and adsorb blue, ultraviolet and infrared light. Nickel chloride ($NiCl_2$) solution will transmit green light and absorb light in other portions of the spectrum. Various water soluble organic dyes can transmit light in portions of the spectrum from ultraviolet to infrared, depending on the individual dye.

I claim:

1. A hand-held device for curing light curable materials, comprising:

a light-tight housing which includes means for permitting the device to be gripped and manipulated in use, and an elongate body part having a removable end wall;

and, within the housing:

a light source which is accessible through said removable end wall of the housing;

a non-imaging light concentrator element having an input end for receiving light from said light source and an output end through which a concentrated beam of light leaves the concentrator element in use; and, means at the output end of the concentrator element for receiving a light guide capable of extending outwardly of the housing for directing light to a target material to be cured;

wherein the light concentrator element has a generally frusto-conical shape, extends about a longitudinal axis and tapers towards said output end, the element having a half cone angle in the range 7 to 12 degrees and including a chamber at said input end for containing a liquid that is selected to both cool the concentrator element and filter out light of a wavelength above a predetermined threshold, the chamber having parallel end faces normal to said axis and a thickness in the range 5 to 21 mm so that light passing through the chamber is refracted towards said axis for concentrating the light;

and wherein said body part of the housing includes a jacket for cooling liquid, said jacket extending around the light source and communicating with said chamber for permitting circulation of liquid through the chamber and the jacket.

2. A device as claimed in claim 1, wherein the light source comprises an elliptical reflector and a bulb located at the focal point of the reflector, the reflector having an outer edge at a maximum diameter of the reflector, and wherein the said chamber comprises a glass panel in abutment with said outer edge of the reflector, and an annular rim around the perimeter of the input end of the concentrator element which is sealed to said glass panel to define said liquid-receiving chamber.

3. A device as claimed in claim 1, wherein said cooling jacket and chamber communicate via conduits which also extend to the exterior of the housing for permitting the cooling liquid to be circulated from the housing for dissipation of heat, and for permitting cooled liquid to be recirculated through said jacket and chamber.

4. A device as claimed in claim 1, further comprising a removable interferential filter at the output end of said frusto-conical light concentrator element.

5. A device as claimed in claim 4, wherein the housing includes a sleeve which surrounds and is coaxial with said output end of the concentrator, said sleeve receiving said interferential filter and providing said means for receiving a light guide.

6. A device as claimed in claim 5, further comprising an externally screw-threaded tube received within said sleeve and coupled thereto by internal screw threads on the sleeve, said tube serving to removably retain said interferential filter and having an inner cylindrical surface dimensioned to receive said light guide.

7. A device as claimed in claim 1, in combination with a light guide received in said means for receiving a light guide and comprising a solid rod which originates as a straight cylindrical section and continues as a curved section towards an output end of the light guide.

8. A device as claimed in claim 7, wherein said rod has a diameter in the range 2–14 mm and the curved section extends about a radius in the range 4–20 cm.

* * * * *